United States Patent [19]
Hamilton

[11] Patent Number: 5,666,664
[45] Date of Patent: Sep. 16, 1997

US005666664A

[54] FACE PROTECTOR SHADE

[76] Inventor: David Thomas Hamilton, 13 Baudin Place, Port Lincoln SA 5606, Australia

[21] Appl. No.: 370,438

[22] Filed: Jan. 9, 1995

[30] Foreign Application Priority Data

Jan. 10, 1994 [AU] Australia .................. PM3298

[51] Int. Cl.$^6$ .................................. A61G 9/00
[52] U.S. Cl. .......................... 2/13; 2/9; 351/47
[58] Field of Search ................. 2/9, 12, 13, 448, 2/449, 15, 10, 11, 426, 427, 429, 431, 438, 450, 454, 424, 206, 173, 207, 447; 351/158, 44, 47

[56] References Cited

U.S. PATENT DOCUMENTS

| 1,582,164 | 4/1926 | Burstyn | 2/206 |
|---|---|---|---|
| 2,364,354 | 12/1944 | Felch | 2/206 |
| 2,541,242 | 2/1951 | Grove | 2/13 |
| 3,298,031 | 1/1967 | Morgan | 2/9 |
| 3,298,032 | 1/1967 | Sielisch | 2/13 |
| 3,299,439 | 1/1967 | Bohner | 351/158 |
| 3,536,385 | 10/1970 | Johnston | 351/47 |
| 3,932,031 | 1/1976 | Johnston | 351/47 |
| 3,991,753 | 11/1976 | Viesca | 2/9 |
| 4,821,340 | 4/1989 | Johnson | 2/13 |
| 4,944,039 | 7/1990 | Dietrich | 2/13 |
| 5,167,036 | 12/1992 | Daprato | 2/13 |
| 5,206,956 | 5/1993 | Olson | 2/13 |
| 5,379,463 | 1/1995 | Schleger et al. | 2/447 |

FOREIGN PATENT DOCUMENTS 688227  2/1940  Germany .................. 2/9

*Primary Examiner*—Michael A. Neas
*Attorney, Agent, or Firm*—Finnegan, Henderson, Farabow, Garrett & Dunner

[57] ABSTRACT

A shade for protection of the lower part of a face, formed from a sheet of plastics material and folded so that the shade can when supported by conventional spectacles shade the temples, cheeks and nose areas. The shade has side apertures to allow for spectacle arms to pass through and be adjustably supported in relative height by the spectacles. The shade has a central nose protector with a clip to engage over the bridge of spectacles so as to hold the two parts together.

15 Claims, 2 Drawing Sheets

FACE PROTECTOR SHADE

The invention described herein relates to a face protector sun shade.

BACKGROUND OF THE INVENTION

The problem to which this invention is directed is the difficulty that hats do not conventionally protect lower parts of the human face from reflected ultraviolet light which can accordingly cause damage to the skin.

On a hot day or in a hot environment a scarf wrapped around the vulnerable lower face is effective for protection but to many people is very inconvenient and as the material is against the skin, insulating and therefore can be very inconvenient.

An object of this invention is to provide means whereby there can be provided a more convenient shade for protection of the lower part of a face.

BRIEF SUMMARY OF THE INVENTION

Accordingly the invention can be said to reside in a face protector shade comprising a sheet folded into a shape constituting:

a nose cover;

two cheek covers; and two side parts adapted to shade the temples each side part having an arrangement facilitating inter engagement with the respective arms of spectacles to provide support thereby for the cover when the spectacles are worn.

In preference the arrangement facilitating inter engagement with the respective arms of spectacles comprises a front substantially vertically extending slot, and a back substantially vertically extending slot; each pair of the slots in a respective side part adapted to have a spectacle arm pass therethrough and the shade to be substantially supported thereby in a shading position when the spectacles are being worn in a conventional manner.

In preference the face protector shade includes:

a nose protecting portion adapted to cover the nose of a person wearing the spectacles to which the face protector shade is attached;

two cheek protecting portions contiguous with either side of the nose protecting portion and adapted to cover the cheeks of the person;

two side parts acting as temple protectors each contiguous with one of the cheek protectors and adapted to cover the temples of the person; and a side flap at the front of each respective side part through which a front slot is positioned.

In preference the back slots are shaped to grippingly engage the spectacle arms and therefore allow for selected different positions of attachment of the face protector shade to the spectacle arms.

In preference the face protector shade includes two upper cheek portions, one upper cheek portion being contiguous with one of the cheek protecting portions and the other upper cheek portion being contiguous with the other cheek protecting portion, wherein the upper cheek portions are adapted to be located behind the base of the eye pieces of the spectacles and the nose protecting portion is adapted to be located in front of the nose piece of the spectacles.

In preference there is a clip adapted to engage the nose protecting portion at one of a selected number of positions and to interengage with a nose bridge of the spectacles to support the protector at a selected position relative to the spectacles.

In a further form of this invention this can be said to reside in a face shade protector comprising a sheet folded to form the above described shapes.

In a further form of this invention this can be said to reside in a face shade protector comprising a sheet folded to form a shape having a central part acting as a nose protecting portion shaped to follow a tapering partially surrounding shape with a lower end larger than an upper end, and extending from a lower end of each side of the central part to form for each side a cheek protector which includes two parts, a shading part which extends forwardly and a supporting part which extends in an approximately vertical orientation from a rear side of the shading part, and extending from an outer side of each respective cheek protector a temple protector which includes at a forward location and also at a rearward location at least one opening through which the arm of the spectacles may pass and provide support for the face shade protector thereby.

In preference the nose protecting portion includes a clip separable from the sheet material and pliable so that by bending the clip can be bent to engage through an aperture in the nose protecting portion and at another end bend over a bridge of the spectacles to support the face shade protector thereby.

In preference, the spectacles to which the face protector shade is adapted to be attached are sunglasses.

DETAILED DESCRIPTION

Figure 1:
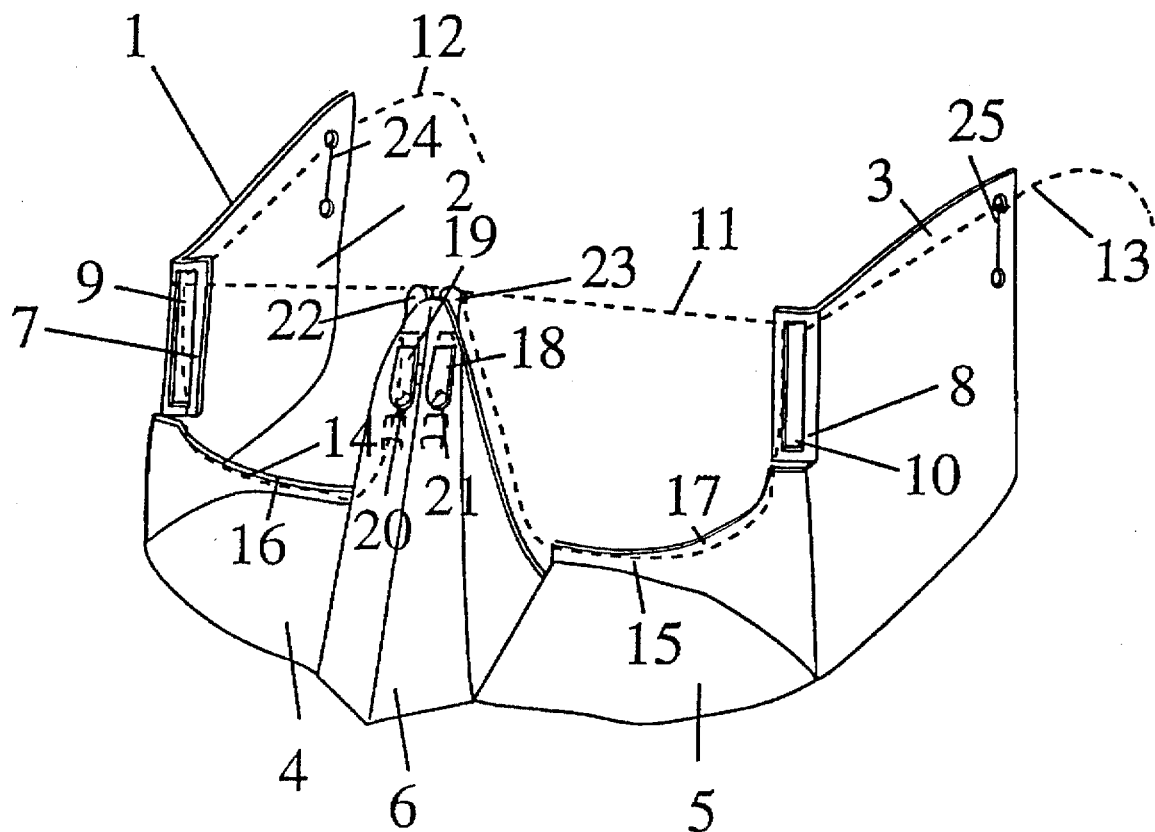
Figure 2:
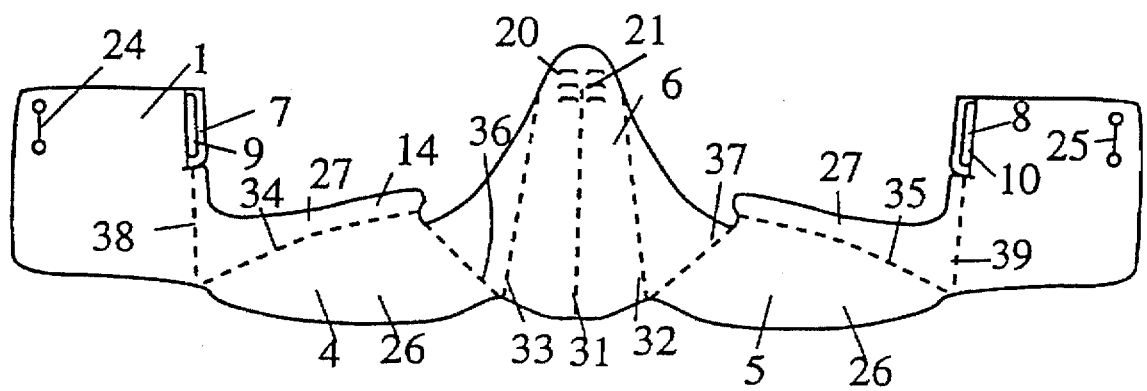
Figure 3:
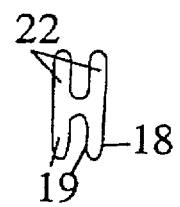

The invention will now be described with reference to a preferred embodiment with assistance of the accompanying drawings wherein:

FIG. 1 which illustrates the embodiment of the face protector shade in a perspective view with the outline of spectacles in dotted outline, FIG. 2 which illustrates the face protector shade as a sheet before it is folded into the shape shown in FIG. 1, and FIG. 3 shows a clip in plan used to clip the shade to the bridge of spectacles Referring to FIG. 1 it will be seen that the face protector shade 1 is made up of parts which are two side parts acting as two temple protectors 2 and 3, two cheek covers acting as cheek protectors 4 and 5 and a nose cover acting as a nose protector 6. Attached to the temple protectors 2 and 3 are inturned front flaps 7 and 8 respectively which have an elongate slot 9 in the one case and 10 in the other in each case wide enough to allow the arm of a spectacle frame 11 to pass therethrough but not to unduly constrain the relative height of the spectacle frame with respect to the protector.

The face protector shade 1 as folded follows substantially the contour of the upper portion of a person's face. A pair of spectacles 11 (which will normally be sunglasses to provide protection from the sun for the eyes of the wearer, are to be threaded through apertures 9 and 10. The arms 12 and 13 of the spectacles frame 11 are threaded through slots 9 and 10. These are arranged then to assume a height and position so that a bottom part 14 and 15 of the lens holding part of the frame 11 will reside behind the nose piece 6, in front of substantially vertical parts 16 and 17.

The overall relative position of the protector is determined by clip 18 formed from an easily malleable metal in this case soft aluminium and having a first two legs 19 passing through slits at 20 or 21 and a further two legs 22 being used to engage over with an interlocking grip a cross frame part or bridge of the spectacle frame 11.

Now referring to the embodiment in further detail a sheet of relatively thin and pliable plastics material in the shape as is shown in plan in FIG. 2 is folded along the lines shown dotted to form a shape as shown in FIG. 1. This has a central part or nose cover 6 acting as a nose protector shaped by folding about fold lines 31, 32 and 33 to follow a tapering partially surrounding shape with a lower end extending over a larger area than an upper end, and extending from a lower end of each side of the central part 6 to form for each side a cheek protector 4 and 5. Each cheek protector 4 and 5 includes two parts, a shading part 26 which extends forwardly and a supporting part 27 which extends to define an approximately vertical alignment from a rear side of the shading part these being achieved by folding about fold lines 34 and 35 and extending contiguously from the nose protector portion through fold lines 36 and 37.

Fold lines 34 and 35 follow a curved path so that when a fold is achieved this causes the shading part 26 to adopt a curved shape which has the advantage of providing an improved appearance and also causes the part to be stiffer.

The supporting part 27 of the cheek protector is contiguously connected to the temple connector through fold line 38 and 39.

In each case the fold line which is shown as a dotted line in the drawing is made in a sheet of plastics material by cutting a continuous cut along the length of the line as shown in the drawing which extends approximately halfway through the thickness of the sheet material.

Extending from an outer side of each respective cheek protector 4 and 5 a side cover acting as a temple protector includes at a forward location and also at a rearward location at least one opening through which the arm of the spectacles may pass and provide support for the face shade protector thereby.

With this arrangement the shade can be used with a large range of different shapes and sizes of sunglasses although it is not suggested that there may not be some sunglasses that do not fit. However in practice it is found that the design described is useful for a reasonable number of designs of sunglasses now available. A feature of the shade includes the fact that the cheek protector with its forwardly extending shading part 26 provides a base upon which the bottom of a sunglasses frame will sit so that the design then allows the arms of spectacles to each be located at a height that has a reasonable range of freedom. This is achieved by having the slot such as at 9 and 10 of sufficient length to allow for this freedom.

Further the use of a slit at the back of the side part allows substantial freedom of position of an arm while still providing for good support for a variety of different sizes and shapes of arms.

Further however by using a clip at the upper end of the nose cover this allows for the shade to be held against the frame of spectacles.

The nose protecting portion includes the clip 18 shown separately in FIG. 3 separable from the sheet material and pliable by being cut from sheet aluminium of an appropriate grade so that by relatively modest manual pressure bending the clip can be achieved to engage with the nose cover through apertures shown as 30 at a selected height in the nose cover otherwise referred to as the nose protecting portion and at another end bent over a bridge of spectacles to hold the face shade protector close to the spectacle frame.

The protector is designed to be made from a flat sheet of moderately pliable plastics material, In either case the arm 12 and the arm 13 passes as well through slit 24 and 25 respectively. This is such that the respective arm is grippingly held by the resilient character of the sheet material passing through the offset sides of the respective slot. Each of the slits 24 and 25 includes an upper and a lower circular aperture to stop extending a fracture line from the slit The arrangement now described provides for a very economically manufactured protector which can be comfortably used with a very wide variety of sunglasses and can in the main be made to fit sufficiently close to the frame to ensure reasonable protection from the sun.

It is economic because it can be manufactured substantially by cutting from a sheet of plastics material. It is comfortable because it is supported by existing spectacles which have been developed for years and therefore are inherently comfortable.

Further, it can provide protection for the prominent parts of a persons face which are often considered to be the most vulnerable to ultraviolet damage which can of course include sunburn but also activate vital diseases such as the virus herpes simplex, or it can cause melanoma.

Unlike sun creams which need to be replaced from time to time, the cover provides constant cover.

As far as its appearance is concerned, the cover can be made to have any chosen pattern or it can be made from clear material in that it is known that clear polyvinylfluoride can provide substantial protection against passage therethrough of ultraviolet protection.

In a further design, there is a pattern of dots covering the otherwise clear material so that there can be vision through the clear material while the density of the dots can be used to create a preferred appearance.

I claim:

1. A face protector shade for use in combination with a pair of spectacles worn by a wearer, said spectacles having a frame portion adapted to be positioned over the nose of a wearer, said frame portion supporting a pair of lens on either side of the nose, and a pair of arms extending rearwardly of the face of the wearer from opposite sides of the frame portion and adapted to be positioned over the ears of the wearer, said face protector shade comprising a flat sheet of pliable material folded into a shape having a nose protecting portion for covering the nose of the wearer, two cheek protecting portions on either side of said nose protecting portion for covering the cheeks of the wearer, each cheek protecting portion comprising an upper cheek portion and a contiguous lower cheek portion, the upper cheek portion extending substantially vertically downward from a bottom part of a lens and the lower cheek portion outwardly from a lower edge of each upper cheek portion, said lower cheek portions being contiguous with the nose protecting portion, and two side portions contiguous with and extending rearwardly of the face of the wearer from an outer side of each upper cheek portion for protecting the temples of the wearer, each side portion having at least one aperture through which an arm of the spectacles can pass so that the spectacles when worn by a wearer support the face protector shade in position on the wearer's face.

2. The face protector shade of claim 1, wherein the nose protecting portion tapers downwardly and outwardly from an upper end to a larger lower end and has a shape that partially surrounds the nose of the wearer, said upper cheek portions of the cheek protecting portions being contiguous with a side of the nose protecting portion and the lower cheek portions with a lower end of each side of the nose protecting portion.

3. The face protector shade of claim 2, including a bendable clip engageable with an upper end of the nose protecting portion and adapted to be bent over the frame of the spectacles adjacent the nose of the wearer to further support the face protector shade in position on the wearer's face.

4. The face protector shade of claim 1, including a vertically extending slot in a front part of each side portion and a vertically extending slit in a rear part of each side portion, each pair of a slot and a slit adapted to have an arm of the spectacles pass therethrough and a clip adapted to engage between an upper end of the nose protecting portion of the shade and the frame of spectacles to further support the face protector shade in position on the face of the wearer.

5. The face protector shade of claim 4, wherein the vertically extending slot is provided in a side flap extending substantially perpendicular from a front edge of each side portion and the slit in the rear part thereof is adapted to grippingly engage a spectacle arm at a rear end of the arm adjacent an ear of the wearer.

6. The face protector shade of claim 1, including a clip engageable with an upper end of the nose protecting portion at a plurality of locations and the frame of the spectacles adjacent the nose of the wearer to support the face protector shade in position on the wearer's face at a selected height relative to the spectacles.

7. The face protector shade of claim 6, wherein the nose protecting portion has a plurality of slits therein adapted to be engaged by the clip.

8. Face protection wear comprising in combination a pair of spectacles to be worn by a wearer, said spectacles having a frame portion adapted to be positioned over the nose of a wearer, said frame portion supporting a pair of lens on either side of the nose, and a pair of arms extending rearwardly of the face of the wearer from opposite sides of the frame portion and adapted to be positioned over the ears of the wearer and a face protector shade comprising a flat sheet of pliable material folded into a shape having a nose protecting portion for covering the nose of the wearer, two cheek protecting portions contiguous with and on either side of said nose protecting portion for covering the cheeks of the wearer, said cheek protecting portions extending substantially from a bottom part of each lens downwardly over the cheeks of the wearer, and two side portions contiguous with and extending rearwardly of the face of the wearer from an outer side of each cheek protecting portion for protecting the temples of the wearer, each side portion having at least one aperture through which an arm of the spectacles extends to secure the face protector shade to the spectacles so that the spectacles when worn by a wearer place the face protector shade in position on the wearer's face.

9. The face protector wear of claim 8, including a vertically extending slot in a front part of each side portion and a vertically extending slit in a rear part of each side portion of the face protector shade, each pair of a slot and a slit having an arm of the spectacles extending therethrough and a clip engaged between an upper end of the nose protecting portion of the shade and the frame of spectacles to further secure the face protector shade to the spectacles.

10. The face protector wear of claim 9, wherein the vertically extending slot is provided in a side flap extending substantially perpendicular from a front edge of each side portion and the slit in the rear part thereof grippingly engages a spectacle arm at a rear end of the arm adjacent an ear of the wearer.

11. The face protector wear of claim 8, wherein each cheek protecting portion comprises an upper cheek portion and a contiguous lower cheek portion, the upper cheek portion extending substantially vertically downward from a bottom part of the lens and the lower cheek portion outwardly from a lower edge of each upper cheek portion, said upper cheek portions of the cheek protecting portions being contiguous with the side portions and the lower cheek portions with the nose protecting portion.

12. The face protector wear of claim 11, including a clip engaged between an upper end of the nose protecting portion at one of a plurality of locations and the frame of the spectacles adjacent the nose of the wearer to secure the face protector shade to the spectacles at a selected height relative to the spectacles.

13. The face protector wear of claim 12, wherein the nose protecting portion has a plurality of slits to provide said plurality of locations.

14. The face protector wear of claim 8, wherein the nose protecting portion tapers downwardly and outwardly from an upper end to a larger lower end and has a shape that partially surrounds the nose of the wearer, and each cheek protecting portion comprises an upper cheek portion and a contiguous lower cheek portion, the upper cheek portion extending substantially vertically downward from a bottom part of the lens and the lower cheek portion outwardly from a lower edge of each upper cheek portion, said upper cheek portions of the cheek protecting portions being contiguous with a side of the nose protecting portion and the lower cheek portions with a lower end of each side of the nose protecting portion.

15. The face protector wear of claim 14, including a bendable clip engaged with an upper end of the nose protecting portion and bent over the frame of the spectacles adjacent the nose of the wearer to further secure the face protector shade to the spectacles.

* * * * *